(12) United States Patent
Ford

(10) Patent No.: US 6,551,277 B1
(45) Date of Patent: Apr. 22, 2003

(54) SYRINGE PUMPS

(75) Inventor: Andrew John Ford, Great Glen (GB)

(73) Assignee: Smiths Group PLC, London (GB)

( * ) Notice: Subject to any disclaimer, the term of this patent is extended or adjusted under 35 U.S.C. 154(b) by 210 days.

(21) Appl. No.: 09/605,870

(22) Filed: Jun. 29, 2000

(30) Foreign Application Priority Data

Jul. 3, 1999 (GB) .............................................. 9915525

(51) Int. Cl.⁷ ............................................. A61M 37/00
(52) U.S. Cl. ...................... 604/131; 604/151; 604/152; 604/153; 604/154; 604/155; 128/218; 340/540; 606/154; 600/561
(58) Field of Search ................................ 604/131, 151, 604/154, 155, 152, 153; 128/218; 340/540; 606/154; 600/561

(56) References Cited

U.S. PATENT DOCUMENTS

| | | | |
|---|---|---|---|
| 4,273,122 A | * 6/1981 | Whitney et al. | 128/218 |
| 4,560,979 A | * 12/1985 | Rosskopf | 340/540 |
| 5,232,449 A | * 8/1993 | Stern et al. | 604/154 |
| 5,501,665 A | 3/1996 | Jhuboo et al. | |
| 5,533,981 A | 7/1996 | Mandro et al. | |
| 5,647,853 A | 7/1997 | Feldmann et al. | |
| 5,656,034 A | * 8/1997 | Kochersperger et al. | 604/155 |
| 5,807,334 A | * 9/1998 | Hodosh et al. | 604/131 |
| 5,814,015 A | 9/1998 | Gargano et al. | |
| 5,879,360 A | * 3/1999 | Crankshaw | 606/154 |
| 6,159,161 A | * 12/2000 | Hodosh | 604/131 |

FOREIGN PATENT DOCUMENTS

| | | |
|---|---|---|
| DE | 42 08 483 | 2/1993 |
| EP | 0 589 356 A2 | 9/1993 |

* cited by examiner

Primary Examiner—Thomas Denion
Assistant Examiner—Theresa Trieu
(74) Attorney, Agent, or Firm—Connolly Bove Lodge & Hutz, LLP; Larry J. Hume

(57) ABSTRACT

A syringe pump has a plunger head retainer with two retainer arms mounted on shafts extending parallel to the syringe axis. Each shaft carries a gear, which is engaged by common gear wheel mounted on a threaded shaft. Initially, the shaft is rotated to displaces the gear and hence the retainer arms axially forwardly, and thereafter swing the retainer arms outwardly to an open position. After the syringe has been loaded in the pump, the plunger head retainer is driven forwards until a pad coupled with a force sensor detects contact with the head. This causes the retainer arms to be swung in across the forward side of the plunger head and to be pulled rearwardly against the plunger head. The pump then reduces the force applied by the retainer arms to ensure that the force sensor can respond to force on the plunger during expulsion of liquid from the syringe.

18 Claims, 4 Drawing Sheets

SYRINGE PUMPS

BACKGROUND OF THE INVENTION

This invention relates to syringe pumps.

Syringe pumps are used to supply medication to a patient from a pre-filled syringe via an infusion line. The syringe pump applies a force to the plunger of the syringe to drive medication into the infusion line at a controlled rate. The head of the plunger is retained in such a way as to allow the plunger to be pushed in but to prevent the plunger moving in of its own accord as a result of siphoning of fluid from the syringe barrel. The plunger head is usually retained by means of wedge-like arms that move across the forward surface of the head and force the rear surface of the plunger head against a forward facing surface on the plunger head retainer so as to clamp it firmly against this surface. Because the size and thickness of plunger heads vary in different syringes, the plunger head retainer may not be able to accommodate all the different heads, thereby restricting the range of syringes with which the pump can be used. If the plunger head retainer does not retain the plunger head securely, it may allow the plunger to move and allow fluid to siphon from the syringe.

It is common to measure the force exerted on the plunger head by the pump driver in order to be able to detect excess force, such as caused by an occlusion. It is an advantage to be able to respond to a low level of excess force without false alarms. The force sensor is, however, usually located relatively remotely of the plunger head so a margin must be allowed for friction and other forces acting on the drive train.

BRIEF SUMMARY OF THE INVENTION

It is an object of the present invention to provide an alternative syringe pump and method of operation.

According to one aspect of the present invention there is provided a syringe pump adapted to receive a syringe of the kind having a plunger movable along a barrel, the pump including a plunger head retainer mechanism having a forwardly-facing surface adapted to engage a rear surface of the plunger head and to apply a forwardly-directed force to the plunger, and the plunger head retainer mechanism including force sensor means responsive to force exerted on the plunger head by the retainer mechanism during displacement of the plunger.

According to a second aspect of the present invention there is provided a syringe pump adapted to receive a syringe of the kind having a plunger movable along a barrel, the pump including a plunger head retainer mechanism including a pad member coupled with the plunger head mechanism via force sensor means, the pad member being adapted to engage a rear surface of the plunger head such that a forwardly-directed force is applied to the plunger via the pad member and such that the force sensor means is responsive to force exerted on the plunger head by the retainer mechanism during displacement of the plunger.

The retainer mechanism is preferably arranged initially to pull the plunger head rearwardly relative to the mechanism, thereby increasing force on the sensor, and is preferably arranged subsequently to relieve the force on the sensor.

According to a third aspect of the present invention there is provided a syringe pump adapted to receive a syringe of the kind having a plunger movable along a barrel, the pump including a plunger head retainer mechanism having a forwardly-facing surface adapted to engage a rear surface of the plunger head and apply a forwardly-directed force to the plunger, the retainer mechanism having at least one retainer member that is movable both laterally and axially so that it can be displaced laterally across the front surface of the plunger head and can be displaced axially rearwardly relative to the mechanism against the front surface of the plunger head.

The retainer mechanism preferably includes a force sensor coupled with the forwardly-facing surface, and the force sensor may be provided by a strain beam supporting a pad exposed on the forwardly-facing surface. Preferably the retainer mechanism includes a spring arranged to urge the pad forwardly. The retainer mechanism is preferably operable such that the or each retainer member is initially displaced axially rearwardly relative to the mechanism to apply force between the rear surface of the plunger head and the forwardly facing surface, the retainer member being subsequently displaced axially forwardly a small distance to reduce the force. The retainer mechanism preferably includes two retainer members located on laterally opposite sides of the plunger. Each retainer member may include an arm extending from a shaft, the shaft extending parallel with the axis of the syringe, such that the arm can be displaced laterally by rotating it about the shaft and such that the or each arm can be displaced axially by moving the shaft along its axis. Each shaft is preferably driven by a gear assembly including a rotatable, threaded shaft and a gear wheel threaded on the shaft such that rotation of the shaft initially moves the gear wheel along the shaft to the end of the shaft and thereafter continued rotation of the shaft rotates the gear wheel. Each shaft may carry a gear, the gear assembly and the gear on each shaft having cooperating flange and channel formations. The pump may include a position sensor arranged to detect a limit of movement of each retainer member.

According to a fourth aspect of the present invention there is provided a method of loading a syringe in a syringe pump comprising the steps of: locating a syringe on the pump with a plunger head retainer in a rear position and with a retainer member on the plunger head retainer in an open position; displacing the plunger head retainer forwardly until it contacts the rear surface of the plunger head; in response to contact with the plunger head, displacing the retainer member initially to a closed position forwardly of the forward surface of the plunger head; and thereafter displacing the retainer member to a rear position in contact with the forward surface of the forward surface of the plunger head.

According to a fifth aspect of the present invention there is provided a method of loading a syringe in a syringe pump comprising the steps of: displacing a plunger head retainer to a rear position; operating a motor in the plunger head retainer in one sense to move a retainer member radially outwardly and axially forwardly; locating a syringe on the pump; displacing the plunger head retainer forwardly until it contacts the rear surface of the head of a plunger of the syringe; rotating said motor in an opposite sense such that the retainer member moves initially to a closed position forwardly of the forward surface of the plunger head and thereafter to a rear position in contact with the forward surface of the forward surface of the plunger head.

According to a sixth aspect of the present invention there is provided a method of operating a syringe pump comprising the steps of: locating a syringe on the pump with a plunger head retainer in a rear position; displacing the plunger head retainer forwardly until it contacts the rear surface of the plunger head; retaining the plunger head with the plunger head retainer such as to prevent forward displacement of the plunger head relative to the retainer but to allow continued monitoring of force applied between the plunger head and the retainer; and advancing the retainer to move the plunger forwards and dispense contents of the syringe whilst monitoring the force between the plunger head retainer and the plunger head.

A syringe pump and its method of operation, according to the present invention, will now be described, by way of example, with reference to the accompanying drawings.

BRIEF DESCRIPTION OF THE INVENTION

DETAILED DESCRIPTION OF THE INVENTION EMBODIMENT

Figure 1:
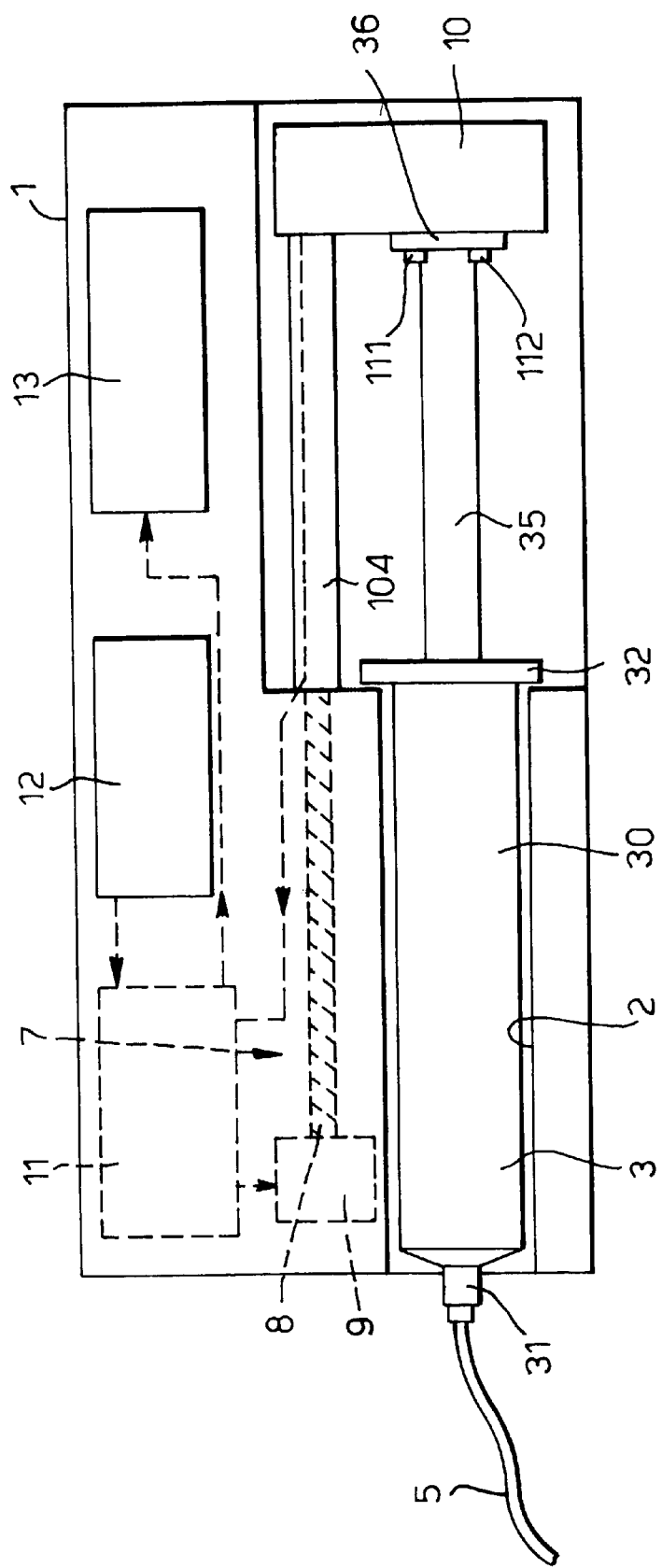
FIG. 1 is a simplified view of the front of the pump.

With reference first to FIG. 1, the pump includes an outer housing 1 with a recess 2 on its front surface shaped to receive a syringe 3 of conventional kind. The syringe 3 has a cylindrical barrel 30 with an outlet or nose 31 at its forward end and a flange or ear 32 at its rear end. The nose 31 is connected to an infusion line 5 so that a medication liquid in the syringe can be dispensed to a patient via the infusion line, by pushing in the plunger 35 of the syringe. The pump has a conventional drive mechanism 7, such as including a lead screw 8 driven by a motor 9, coupled with a novel retainer mechanism 10 for engaging the head 36 of the plunger 35. The motor 9 is driven by a control unit 11, which receives inputs from a keypad 12, or other user input means, and various sensors. The control unit 11 also provides an output to a display 13.

Figure 2:
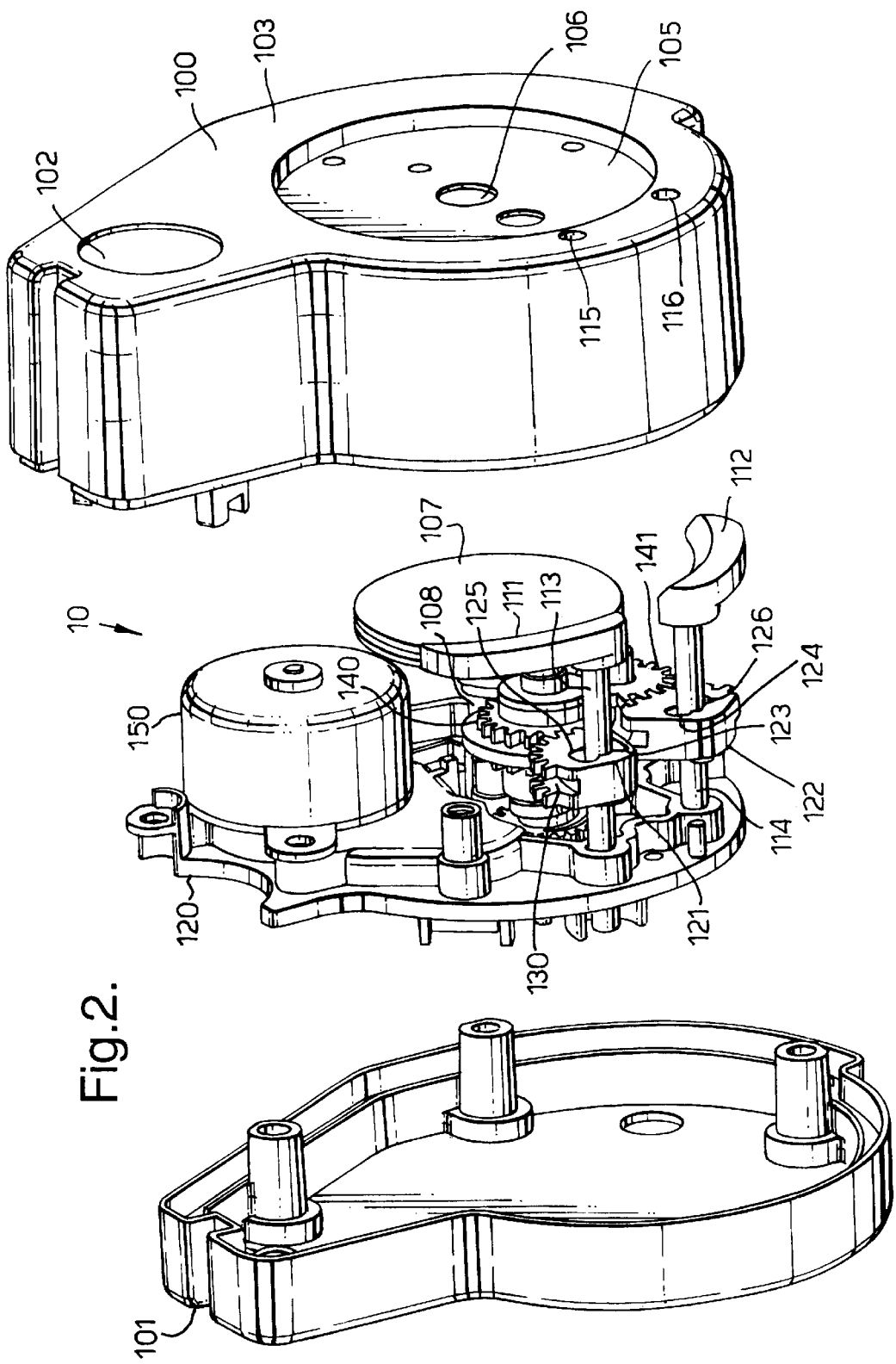
FIG. 2 is a perspective, exploded view of the plunger head retainer mechanism of the pump from below.
Figure 3:
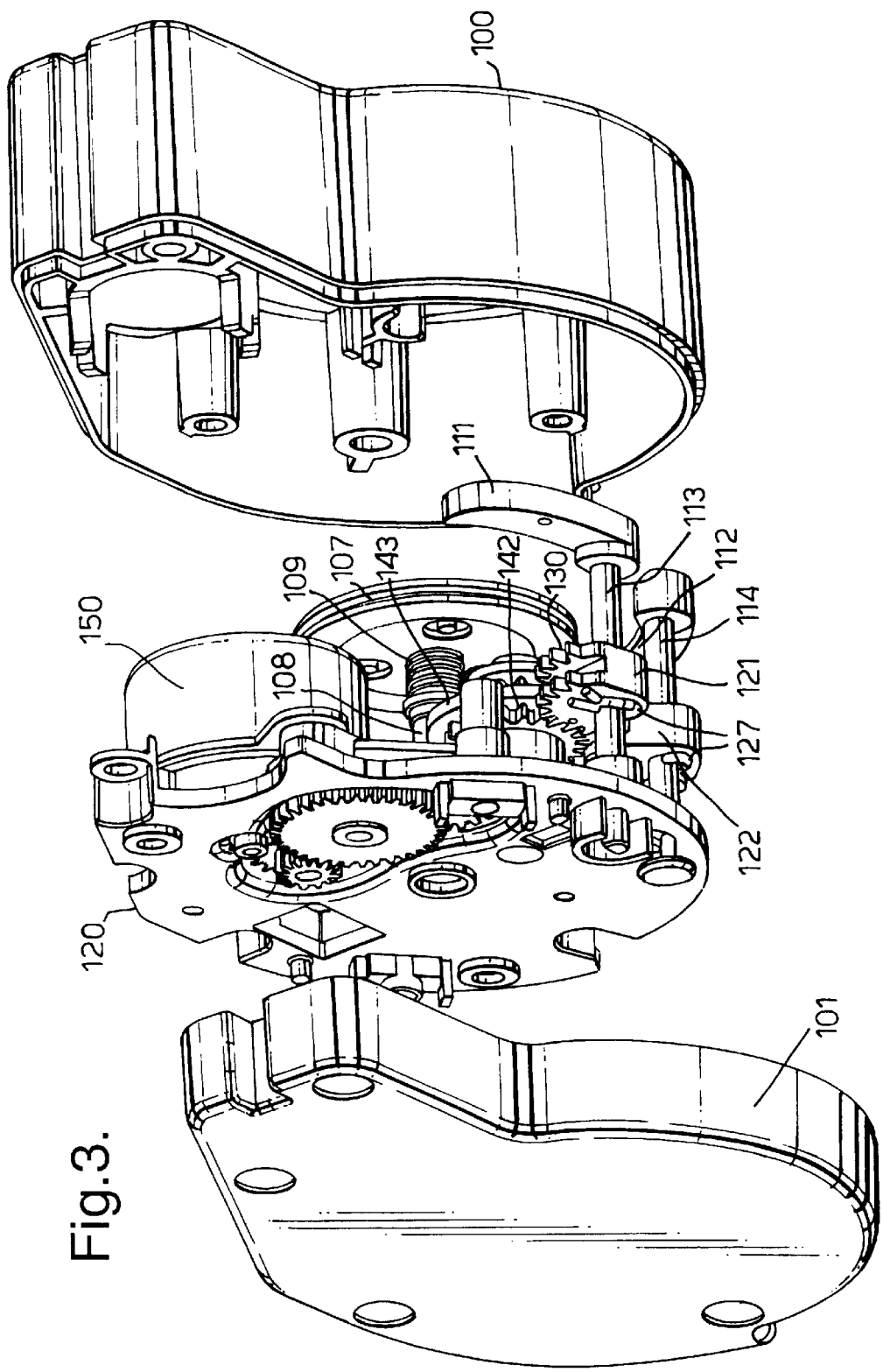
FIG. 3 is a perspective, exploded view of the plunger head retainer mechanism of the pump from the rear side.

With reference now also to FIGS. 2 and 3, the plunger head retainer mechanism 10 has an outer casing provided by a forward part 100 and a rear part 101. The forward part 100 has a circular hole 102 on its outer face 103 towards its edge, in which is received a tubular sleeve 104 extending parallel with the syringe 3. The sleeve 104 is mounted axially about the leadscrew 8 so that rotation of the leadscrew displaces the sleeve and retainer mechanism 10 axially forwards or backwards.

The front face 103 of the casing also has a larger, shallow, circular recess 105 with a central aperture 106. In the recess 105 is located a circular pad 107 having a rearwardly-extending force sensor in the form of a strain beam 108 projecting through the aperture 106 inside the casing. For clarity, FIGS. 2 and 3 show the pad 107 mounted on the internal components of the mechanism 10 although, in practice, it is located on the external surface of the forward casing part 100. The pad 107 is resiliently urged axially outwardly by a coil spring 109 around the strain beam 108. The strain beam 108 provides an output to the control unit 11 representative of axial pressure on the pad 107.

Two arms 111 and 112 extend parallel with the front face 103 and are spaced a short distance forwardly of the face. The arms 111 and 112 are curved along their length along an arc generally coaxial, in their rest position, with the pad 107. The arms 111 and 112 are mounted on respective shafts 113 and 114 extending parallel to the axis of the syringe 3 and projecting through bushes 115 and 116 in the front face 103 of the casing, towards one edge. The rear ends of the shafts 113 and 114 are journalled with a base plate 120 extending laterally within the retainer mechanism 10. The shafts 113 and 114 are movable axially along their length as well as being able to rotate about their axes. Each shaft 113 and 114 carries a segment gear 121 and 122 mounted on the shafts by means of a hole with a butterfly-shape slot 123 and 124 in the gears. The shafts 113 and 114 each carry two radially-extending pins 125 and 126 located in the slots 123 and 124 so that the gears 121 and 122 are rotatable relative to the shafts through a small angle, as limited by the engagement of the pins with the opposite sides of the slots. A clip 127 is secured to each shaft on one side of the gears to prevent axial movement of the gears in one direction along the shafts— movement in the other direction being prevented by the pins 125 and 126. A spring (not shown) is secured to the clip 127 on each shaft 113 and 114 to apply a resilient force urging one shaft 113 to rotate in a clockwise sense relative to the front face 103 of the casing and urging the other shaft 114 in the opposite sense. Thus, the springs urge the arms 111 and 112 to swing inwardly towards one another.

Figure 4:
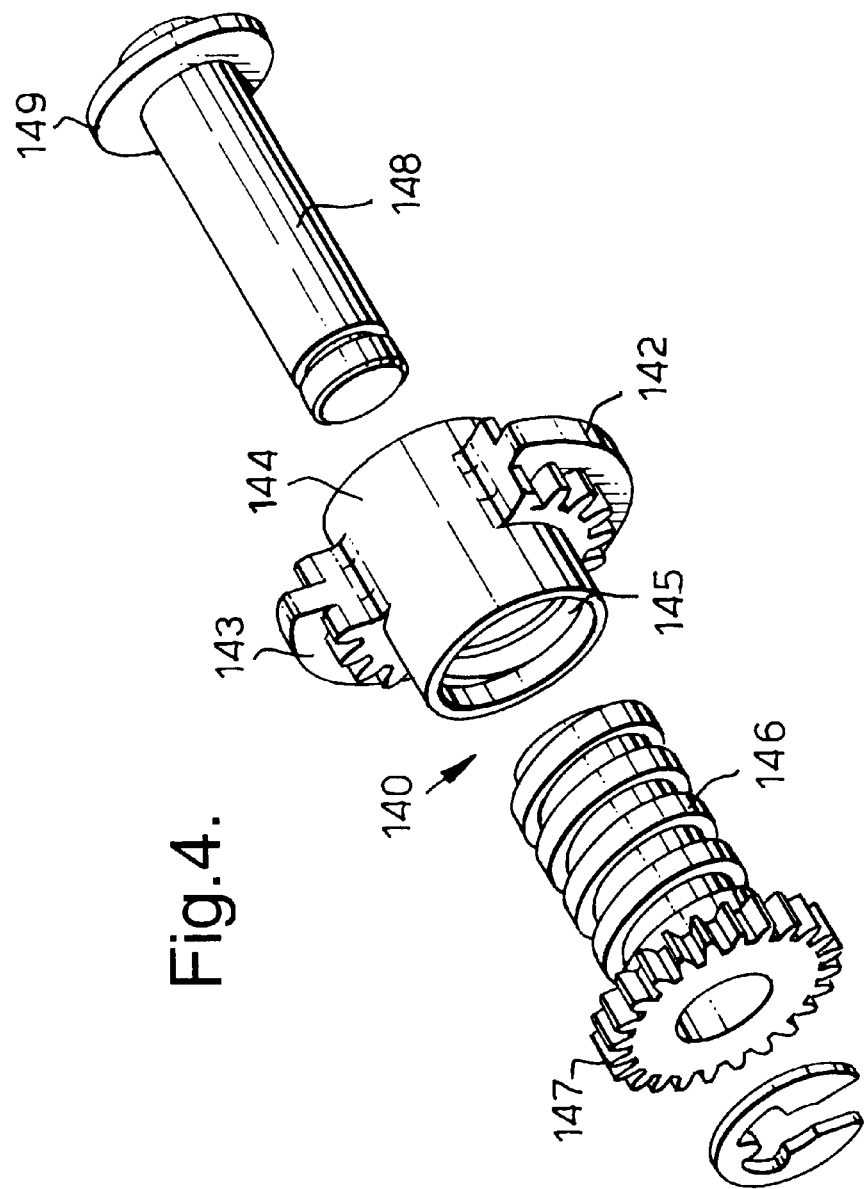
FIG. 4 is an enlarged perspective view of a sub-assembly within the retainer mechanism.

The segment gears 121 and 122 each have a channel 130 around the toothed edge of the gear dividing into two parallel spaced segments. One segment gear 121 is engaged directly by a central gear sub-assembly 140, whereas the other gear 122 is engaged by an idler gear 141 driven from the central gear assembly. The central gear sub-assembly 140 is shown most clearly in FIG. 4. The gear sub-assembly has a circular gear wheel 142 with a flange 143 projecting radially midway along its length. The flange 143 is shaped to fit within the channel 130 in the segment gear 121. The gear wheel 142 is fixed on a boss 144 having a helical thread 145 of square profile around its inner surface. The central gear sub-assembly 140 also includes a hollow shaft 146 with a helical thread on its outer surface, which matches and engages the thread 145 on the inside of the boss 144. At its rear end, the shaft 146 has a spur gear 147, the spur gear and shaft being free to rotate on an internal spindle 148 having a flange 149 at its forward end. The central gear sub-assembly 140 is mounted on the base plate 120 with the shaft 146 extending parallel to the syringe axis. The spur gear 147 engages a gear train coupled with an electric motor 150 within the plunger head retainer mechanism 10. It can be seen that rotation of the spur gear 147 would cause movement of the gear wheel 142 along the threaded shaft 146 if rotation of the gear wheel were prevented, the extent of displacement being limited by the length of the shaft. The retainer mechanism 10 also includes a sensor (not shown) responsive to the angular position of the arms 111 and 112, or the shafts 113 and 114, and located to sense when the arms have moved to their extreme outward position.

Initially, the motor 150 is rotated forwardly to rotate the spur gear 147 and the threaded shaft 146 clockwise and thereby jack the gear wheel 142 forwardly along the shaft. This forward movement of the gear wheel 142 also moves the segment gears 123 and 124 forwardly and hence moves the arms 111 and 112 forwardly. When the gear wheel 142 reaches its maximum extent of movement along the threaded shaft 146, as limited by engagement with the flange 149, continued rotation of the shaft causes the gear wheel to rotate clockwise. This in turn causes the idler gear 141 to rotate anticlockwise so that the segment gears 121 and 122 are rotated anticlockwise and clockwise respectively, which thereby swings the arms 111 and 112 open. The arms 111 and 112 swing open until the arm position sensor detects they are at their fully open, at which time the control unit 11 stops driving the motor 150 forwardly.

The retainer mechanism 10 is now ready to receive the syringe plunger head 36. The syringe 3 is loaded in the pump and the motor 9 is powered to rotate the leadscrew 8 relatively rapidly, so as to drive the plunger head retainer mechanism 10 forwardly until the pad 107 contacts the rear surface of the plunger head 36. Initial contact is sensed by an optical detector (not shown), which, when tripped, slows forward movement of the retainer mechanism 10 until the strain beam registers a small strain. This causes the control unit 11 to stop further rotation of the leadscrew 8 and causes the motor 150 in the plunger head retainer mechanism 10 to be powered in the reverse direction. This rotates the threaded shaft 146 in an anticlockwise sense so that the gear wheel 142 is also rotated anticlockwise, which in turn rotates the idler gear 141 clockwise. The anticlockwise rotation of the gear wheel 142 and the clockwise rotation of the idler gear 141 cause the segment gears 121 and 122 to rotate clockwise and anticlockwise respectively. The spring force causes the arms 111 and 112 to swing in together to a closed position. The arms 111 and 112 swing together until they contact the shaft of the plunger 35, which prevents further rotation of the arms. The slots 123 and 124 in the segment gears 121 and 122 allow them to rotate further through a few degrees until a part of the gear wheel contacts a stop on the forward part 100 of the casing, thereby preventing further rotation of the central gear wheel. The slots 123 and 124 in the segment gears enable the arms 111 and 112 to stop in a partially closed position (limited by engagement with the plunger shaft) whilst ensuring that they are swung back to the fully open position when the motor direction is reversed.

Continued rotation of the threaded shaft 146 by the motor 150 causes the gear wheel 142 to be pulled down the shaft, the arms 111 and 112 also being pulled down because of the engagement of the flanges 143 in the channels 130 of the segment gears 121 and 122. The arms 111 and 112 are, therefore, pulled rearwardly until they engage the forward surface of the plunger head 36. When this happens, the plunger head 36 is pulled rearwardly relative to the retainer mechanism 10, against the forward surface of the pad 107 causing an increase in pressure on the strain beam 108. When this increase in pressure is sensed, the pump control unit 11 stops the motor 150 and reverses it a few steps to give a predetermined clearance between the rear surface of the pad 107 and the floor of the recess 105. The leadscrew 8 is then rotated in the normal way to move the retainer mechanism 10, and hence the plunger 35, forwardly to dispense the contents of the syringe 3 at the required rate.

Because the plunger head 36 is coupled with the retainer mechanism 10 via the pad 107 and the strain beam 108, and because there is a clearance between the rear surface of the pad and the floor of the recess 105, the strain beam is responsive to pressure exerted by the retainer mechanism on the plunger 35 while the plunger is actually being displaced to expel medication from the syringe 3. If there should be an occlusion in the infusion line 5, or if the syringe 5 should jam, there would be an immediate increase in pressure on the strain gauge 110. Because the arrangement of the present invention enables pressure on the plunger to be measured directly, the apparatus can be sensitive to small increases in pressure.

The plunger head retainer mechanism can be used with a wide variety of plunger heads because the action of spacing the retainer arms and subsequently pulling them back to clamp the head allows for wide variation in the size and shape of head.

What I claim is:

1. A syringe pump adapted to receive a syringe of the kind having a plunger movable along a barrel, the pump comprising: a location for said syringe; a syringe drive mechanism; and a plunger head retainer mechanism, said retainer mechanism including a pad member and a force sensor, said force sensor coupling said pad member with said retainer mechanism, wherein said pad member is adapted to engage a rear surface of a head of the plunger such that a forwardly-directed force is applied to the plunger via the pad member and such that said force sensor is responsive to force exerted on the plunger head by the retainer mechanism during displacement of the plunger.

2. A syringe pump adapted to receive a syringe of the kind having a plunger movable along a barrel, the pump comprising;
   a location for said syringe;
   a syringe drive mechanism; and
   a plunger head retainer mechanism,
   said retainer mechanism including a forwardly-facing surface adapted to engage a rear surface of a head of the plunger and to apply a forwardly-directed force to the plunger,
   wherein the plunger head retainer mechanism includes a force sensor responsive to force exerted on the plunger head by the retainer mechanism during displacement of the plunger,
   wherein the retainer mechanism is arranged to pull the plunger head initially rearwardly relative to the retainer mechanism, thereby increasing force on said sensor, and is arranged subsequently to relieve the force on said sensor.

3. A syringe pump adapted to receive a syringe of the kind having a plunger movable along a barrel, the pump comprising:
   a location for the syringe;
   a syringe drive mechanism; and
   a plunger head retainer mechanism,
   said retainer mechanism having a forwardly-facing surface adapted to engage a rear surface of a head of the plunger and apply a forwardly-directed force to the plunger, a force sensor coupled with said forwardly-facing surface, and at least one retainer member that is movable both laterally and axially so as to be displaceable laterally across a front surface of the plunger head and displaceable by the drive mechanism axially rearwardly relative to the retainer mechanism against a front surface of the plunger head.

4. A syringe pump according to claim 3, wherein the force sensor is provided by a strain beam supporting a pad exposed on said forwardly-facing surface.

5. A syringe pump according to claim 4, wherein the retainer mechanism includes a spring arranged to urge the pad forwardly.

6. A syringe pump according to claim 3, wherein said retainer mechanism is operable such that the retainer member is initially displaced axially rearwardly relative to the retainer mechanism to apply force between a rear surface of said plunger head and said forwardly-facing surface, and wherein the retainer mechanism is subsequently displaced axially forwardly a small distance to reduce said force.

7. A syringe pump according to claim 3, wherein said retainer mechanism includes two said retainer members located on laterally opposite sides of said plunger.

8. A syringe pump according to claim 3, wherein said retainer mechanism includes an electric motor coupled with said retainer member.

9. A syringe pump according to claim 3 including a position sensor arranged to detect a limit of movement of said retainer member.

10. A syringe pump adapted to receive a syringe of the kind having a plunger movable along a barrel, the pump comprising:
- a location for the syringe;
- a syringe drive mechanism; and
- a plunger head retainer mechanism,
- said retainer mechanism having a forwardly-facing surface adapted to engage a rear surface of a head of the plunger and apply a forwardly-directed force to the plunger, and at least one retainer member that is movable both laterally and axially so that it can be displaced laterally across the front surface of the plunger head and can be displaced axially rearwardly relative to the retainer mechanism against a front surface of the plunger head,
- wherein the retainer member includes an arm extending from a shaft, and wherein said shaft extends parallel with an axis of the syringe, such that the arm can be displaced laterally by rotating it about the shaft.

11. A syringe pump according to claim 10, wherein the arm is displaced axially by moving the shaft along its axis.

12. A syringe pump according to claim 10, wherein the retainer mechanism includes a gear assembly coupled with said shaft, said gear assembly including a rotatable, threaded shaft and a gear wheel threaded on said threaded shaft such that rotation of said threaded shaft initially moves the gear wheel along said threaded shaft to its end and thereafter continued rotation of said threaded shaft rotates the gear wheel.

13. A syringe pump according to claim 12, wherein the said shaft of said retainer member carries a gear, and wherein said gear assembly and the said gear on said shaft have cooperating flange and channel formations.

14. A syringe pump adapted to receive a syringe of the kind having a plunger movable along a barrel, the pump comprising: a location for said syringe; a syringe drive mechanism; and a plunger head retainer mechanism, said retainer mechanism including two arms, a motor coupled with said arms and operable to swing the arms across a rear surface of a head of the plunger and to pull the arms rearwardly relative to the mechanism, a pad member and a force sensor, said force sensor coupling said pad member with said retainer mechanism, wherein said pad member is located to engage a rear surface of a head of the plunger when said arms are pulled rearwardly, and wherein said force sensor is responsive to force exerted on the plunger head by the retainer mechanism during displacement of the plunger such that the force sensor is responsive to any obstruction to displacement of the plunger.

15. A method of loading a syringe in a syringe pump comprising:
- locating a syringe on the pump with a plunger head retainer in a rear position and with a retainer member on the plunger head retainer in an open position;
- displacing the plunger head retainer forwardly until it contacts a rear surface of a plunger head of the syringe;
- in response to an output from a force sensor in contact with the plunger head, displacing the retainer member initially to a closed position forwardly of a forward surface of the plunger head; and
- thereafter, displacing the retainer member to a rear position in contact with the forward surface of the plunger head.

16. A method of loading a syringe in a syringe pump comprising the steps of: displacing a plunger head retainer to a rear position; operating a motor in the plunger head retainer in one sense to locate a retainer member radially outwardly and axially forwardly; locating a syringe on the pump; displacing the plunger head retainer forwardly until it contacts a rear surface of a head of a plunger of the syringe; rotating said motor in an opposite sense such that the retainer member moves initially to a closed position forwardly of a forward surface of the plunger head and thereafter to a rear position in contact with the forward surface of the forward surface of the plunger head.

17. A method of operating a syringe pump, comprising:
- locating a syringe on the pump with a plunger head retainer in a rear position;
- displacing the plunger head retainer forwardly until it contacts a rear surface of a plunger head of the syringe;
- retaining a head of a plunger of the syringe with the plunger head retainer to prevent forward displacement of the plunger head relative to the retainer but allowing continued monitoring of force applied between the plunger head and the retainer;
- advancing the retainer to move the plunger forward and dispense contents of the syringe; and
- monitoring the force applied between the plunger head retainer and the plunger head while advancing the retainer to move the plunger forward and dispense contents of the syringe.

18. A syringe pump adapted to receive a syringe of the kind having a plunger movable long a barrel, the pump comprising:
- a location for said syringe;
- a syringe drive mechanism; and a plunger head retainer mechanism,
- said retainer mechanism including a pad member and a force sensor,
- said force sensor coupling said pad member with said retainer mechanism,
- wherein said pad member is adapted to engage a rear surface of ahead of the plunger such that a forwardly-directed force is applied to the plunger via the pad member and such that said force sensor is responsive to force exerted on the plunger head by the retainer mechanism during displacement of the plunger,
- wherein the retainer mechanism is arranged to pull the plunger head initially rearwardly relative to the retainer mechanism, thereby increasing force on said sensor, and is arranged subsequently to relieve the force on said sensor.

* * * * *